United States Patent [19]

Slavtcheff et al.

[11] Patent Number: 5,484,597
[45] Date of Patent: Jan. 16, 1996

[54] CLEAR HYDROALCHOLIC COSMETIC MICROEMULSIONS

[75] Inventors: Craig S. Slavtcheff, Cheshire; Stephen R. Barrow, Trumbull, both of Conn.

[73] Assignee: Chesebrough-Pond's USA Co., Greenwich, Conn.

[21] Appl. No.: 99,879

[22] Filed: Jul. 30, 1993

[51] Int. Cl.$^6$ .................. A61K 7/46; A61K 7/00
[52] U.S. Cl. ............... 424/401; 514/937; 514/938
[58] Field of Search .................. 424/401; 514/937, 514/938

[56] References Cited

U.S. PATENT DOCUMENTS

| | | | |
|---|---|---|---|
| 4,797,273 | 1/1989 | Linn et al. | 424/59 |
| 4,835,002 | 5/1989 | Wolf et al. | 426/590 |
| 4,883,659 | 11/1989 | Goodman et al. | 424/78.03 |
| 4,900,542 | 2/1990 | Parrotta, Jr. et al. | 424/66 |
| 4,940,577 | 7/1990 | Greensberg et al. | 424/59 |
| 4,981,845 | 1/1991 | Pereira | 514/657 |
| 5,030,374 | 7/1991 | Tranner | 252/90 |
| 5,160,739 | 11/1992 | Kanga | 424/401 |
| 5,162,378 | 11/1992 | Guthhauser | 514/785 |
| 5,190,915 | 3/1993 | Behan et al. | 512/2 |
| 5,249,815 | 10/1993 | Faryniarz et al. | 424/47 |
| 5,336,432 | 8/1994 | Petchul et al. | 252/186.28 |
| 5,374,614 | 12/1994 | Behan et al. | 512/3 |

FOREIGN PATENT DOCUMENTS 0261351 3/1983 European Pat. Off. .
0571677 12/1993 European Pat. Off. .

OTHER PUBLICATIONS

Prince, L., in "Microemulsions, Theory and Practice" (L. Prince, Ed.), pp. 32, 48, 120, 121 Academic Press, Inc., New York, N.Y. 1977.
McCutcheon's Emulsifiers & Detergents, International Edition; The Manufacturing Confectioner Publishing Co., vol. 1: pp. 44, 71 (1992).
International Search Report.
Chemical Abstract—vol. 92, No. 10, Mar. 10, 1980; Abstract No. 82190.
Wackherr Technical Bulletin Published 1993.

*Primary Examiner*—Robert E. Sellers
*Assistant Examiner*—Robert H. Harrison
*Attorney, Agent, or Firm*—Milton L. Honig

[57] ABSTRACT

A hydroalcoholic microemulsion composition is provided which includes water, a $C_1$–$C_4$ alkanol and an oil material selected from vitamin oils, $C_{10}$–$C_{60}$ terpenes and mixtures thereof. The composition is formed into a clear, storage stable microemulsion through a combination of surfactants including an ethoxylated castor oil and a propoxylated alkyl ether. Especially useful is a combination of PEG-40 hydrogentated castor oil with either PPG-10 cetyl ether, PPG-10 butanediol or PPG-14 butyl ether.

7 Claims, No Drawings

CLEAR HYDROALCHOLIC COSMETIC MICROEMULSIONS

BACKGROUND OF THE INVENTION

1. Field of the Invention

The invention concerns a hydroalcoholic microemulsion containing vitamin and essential oils which exhibits excellent physical stability and clarity.

2. The Related Art

A clear, skin care product that contains water and alcohol conveys a sense of purity to the consumer. The presence of alcohol also imparts quick drying and cooling sensation characteristics. The use of alcohol is also important for many therapeutic products as it will solubilize certain organic acids such as salicylic acid. Antimicrobial activity is a further benefit.

Many therapeutic cosmetic ingredients are water-insoluble, e.g. vitamins and essential oils. These water-insoluble ingredients require them to be emulsified into a water phase in order to be effectively delivered to the skin. Emulsions tend to be opaque or white because of the large droplet size. Microemulsions consist of micelles of a monolayer of surfactant surrounding an oil droplet. These micelles are small enough so that they do not appreciably diffract light producing a clear product. Alcohol is known to prevent the formation of both emulsions and micelles; indeed, alcohol is commonly used to break emulsions. Formation of a microemulsion that is stable in a hydroalcoholic system is, therefore, quite difficult. Furthermore, the vitamin oils, in particular, are very difficult to form microemulsions with.

Accordingly, it is an object of the present invention to provide a hydroalcoholic microemulsion that is both quick drying and imparts a cooling sensation.

It is another object of the present invention to provide a hydroalcoholic microemulsion wherein the micelles are sufficiently small so they do not appreciably diffract light, thereby producing a clear product.

It is still another object of the present invention to provide a hydroalcoholic microemulsion wherein vitamin oils and terpenes are emulsified to achieve not only a clear product but one that is storage stable.

These and other objects of the present invention will become more readily apparent from consideration of the following summary, detailed description and examples which follow.

SUMMARY OF THE INVENTION

A cosmetic microemulsion composition is provided that includes:

(i) from about 1 to about 99% water;

(ii) from about 1 to about 99% of a $C_1$–$C_4$ alkanol;

(iii) from about 0.1 to about 20% of an oil selected from the group consisting of vitamin oils, $C_{10}$–$C_{60}$ terpenes and mixtures thereof;

(iv) from about 0.1 to about 20% of castor oil ethoxylated with about 30 to about 55 of ethylene oxide per mole of castor oil; and (v) from about 0.1 to about 20% of a $C_4$–$C_{20}$ mono- or dihydric alkanol propoxylated with about 5 to about 50 moles of propylene oxide per mole of alkanol.

DETAILED DESCRIPTION

Now there has been found a hydroalcoholic cosmetic microemulsion of good clarity and stability that suspends vitamin oils and $C_{10}$–$C_{60}$ terpenes. The discovery is based upon the use of a combination of a ethoxylated, hydrogenated castor oil and at least one propoxylated alkyl ether.

Accordingly, a first critical component of compositions according to the present invention is an ethoxylated castor oil, preferably an ethoxylated hydrogenated castor oil. The moles of ethylene oxide per mole of castor oil will range from about 30 to about 55, preferably between about 37 and about 43, optimally about 40 moles of ethylene oxide. Amounts of the ethoxylated castor oil will range from about 0.1 to about 20%, preferably from about 1 to about 10%, optimally from about 2 to about 5% by weight of the composition. Most preferred is PEG-40 hydrogentated castor oil.

A second critical component of compositions according to the present invention is that of a propoxylated alkyl ether. The ether will be based upon a $C_4$–$C_{20}$ mono- or dihydric alkanol. Most preferred are the propoxylated butyl and cetyl alcohols and butanediols. The amount of propylene oxide per mole of alkanol will range from about 5 to about 50, preferably from about 8 to about 20, optimally from about 8 to about 12 moles propylene oxide. Amounts of the propoxylated alkyl ether will range from about 0.1 to about 20%, preferably from about 1 to about 10%, optimally from about 2 to about 5% by weight of the composition. Most preferred are the species PPG-10 cetyl ether and PPG-14 butyl ether and PPG-10 Butanediol.

The hydroalcoholic microemulsion compositions of the present invention will also include water in amounts from about 1 to about 99%, preferably from about 25 to about 75%, optimally from about 30 to about 60% by weight.

Alcohols suitable for the hydroalcoholic microemulsion compositions of the present invention will be the $C_1$–$C_4$ monohydric alkanols. Most preferred is ethanol. The monohydric alkanols will be present in amounts from about 1 to about 99%, preferably from about 15 to about 70%, optimally from about 25 to about 55% by weight.

Another component of the hydroalcoholic microemulsion compositions of the present invention will be that of a skin nutritive oil material. The material will be selected from the group, consisting of vitamin oils, $C_{10}$–$C_{60}$ terpenes and mixtures thereof. Levels of these materials may range from about 0.1 to about 20%, optimally between about 1 and 3% by weight.

Representative of the vitamin oils are vitamin A palmitate, vitamin E linoleate, vitamin E acetate and combinations thereof. The $C_{10}$–$C_{60}$ terpene may be either a hydrocarbon or oxygenated derivative thereof. The terpene may be a monoterpene, a sesquiterpene, a diterpene or triterpene. Representative of the hydrocarbon terpenes are limonene, pinene, myrcene, caryophyllene, farnesene, lycopene, squalene, zingiberene, carotene, camphene, cedrene and mixtures thereof. Representative of the oxygenated terpenes are genial, farnesol, linalool, citronellal, menthol, carvone, camphor, nerol, neral, geranial, thujone, isonorborneol, isoborneol, phytol, bisabolol and mixtures thereof.

Hydroalcoholic microemulsion compositions of the present invention may include or be included with a variety of other cosmetic components. These components are described below.

The first category is represented by $C_7$–$C_{30}$ β-hydroxy carboxylic acids and their salts. Illustrative of this category is salicylic acid as well as the alkalimetal and ammonium salts thereof. Suitable amounts of salicylic acid or salt forms may range from about 0.1 to about 10%, preferably between about 0.8 and about 2.5%, optimally between about 1 and 1.5% by weight.

The second category of keratolytic agent is represented by $C_1$–$C_{25}$ α-hydroxy carboxylic acids of Formula I, having the structure:

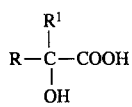

$$R-\underset{OH}{\overset{R^1}{C}}-COOH \qquad (I)$$

wherein R and $R^1$ are H, F, Cl, Br, alkyl, aralkyl or aryl groups of saturated or unsaturated, isomeric or nonisomeric, straight or branched chain, having 1 to 25 carbon atoms, or cyclic form having 5 or 6 ring members, and in addition, R and $R^1$ may carry OH, CHO, COOH and alkoxy groups having 1 to 9 carbon atoms, the α-hydroxyacid existing as a free acid or lactone form, or in salt form with an organic amine base or an inorganic alkali, and as stereoisomers, and D, L, and DL forms when R and $R^1$ are not identical.

Most preferred of this group of materials are glycolic acid, lactic acid and 2-hydroxyoctanoic acid and salts thereof. The salts may be selected from alkalimetal, ammonium and $C_1$–$C_{20}$ alkyl or alkanol ammonium counterions. Levels of α-hydroxyalkanoic acids may range from about 0.1 to about 10%, preferably between about 0.2 and 1%, optimally between about 0.4 and 0.5% by weight.

In a particularly preferred embodiment, there will be present a mixture of both a β-hydroxy carboxylic acid and an α-hydroxy carboxylic acid. For instance, the optimum combination is a mixture of salicylic acid and glycolic acid in a relative weight ratio from about 20:1 to about 1:20, preferably from about 10:1 to 1:1, optimally from about 3:1 to about 2:1.

A still further component of compositions according to the present invention may be $C_1$–$C_{10}$ alkyl lactates. Most preferred is ethyl lactate which may be present in amounts ranging from about 0.01 to about 5%, preferably between about 0.5 and 3%, optimally between about 1.5 and 2.5% by weight.

Antimicrobial agents may also be useful in compositions of the present invention. Typically the antimicrobial agent may be material such as triclosan tricarbanilide, tea tree oil, farnesol, farnesol acetate, hexachlorophene, $C_4$–$C_{20}$ quaternary ammonium salts such as benzolconium chloride and a variety of zinc or aluminum salts. Typically the zinc or aluminum salts are compounds such as zinc pyridinethione, zinc sulphate, zinc chloride, zinc phenolsulphonate, aluminum chloride, aluminum sulphate and aluminum chlorhydrate. Amounts of the astringent may range from about 0.1 to about 5%, preferably from about 0.2 to about 1%, optimally about 0.3% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerot poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Humectants of the polyhydric alcohol-type may also be included in the compositions of this invention. The humectant aids in increasing the effectiveness of the emollient, reduces scaling, stimulates removal of built-up scale and improves skin feel. Most especially for purposes of this invention, polyhydric alcohols enhance penetration of water-phase dissolved actives (e.g. the hydroxycarboxylic acids, alkyl lactates and antimicrobials). Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners/viscosifiers in amounts up to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B. F. Goodrich under the Carbopol trademark.

Cosmetic compositions of the present invention may be included in many product forms. These forms may include lotions, creams, sticks, roll-on formulations, mousses, aerosol sprays, pad-applied formulations, and overnight, peelable facial masks.

A particularly preferred embodiment of the present invention is that the hydroalcoholic microemulsion compositions be incorporated into a quick-drying gel or paste that forms a peelable facial mask. A film-forming and an adhesion promoting polymer are necessary in this product form. Polyvinyl alcohol can serve as the film-forming polymer. Preferably the polyvinyl alcohol will be present as a low and high molecular weight species. The former will have a number average molecular weight ranging from about 15,000 to 27,000. The higher polyvinyl alcohol material will have a number average molecular weight ranging from about 44,000 to 65,000. These materials are available from the Air Products Company under the trademark, Airvol 205S® and Airvol 523®. Amounts of total polyvinyl alcohol will range from about 2 to about 40%, preferably from about 10 to about 20%, optimally between about 10 and 15% by weight. The ratio of low to high molecular weight may range from about 1:20 to 20:1, preferably from about 1:10 to 1:1, optimally from about 1:5 to 1:3, respectively.

As the adhesion promoting polymer, it is preferable to employ a hydrophobic acrylate or methacrylate polymer. Especially useful is Pemulen TR2® from the B. F. Goodrich Company. The CTFA name is acrylates/$C_{10}$–$C_{30}$ alkyl acrylate cross-polymer. The adhesion-promoting polymer will be present in amounts from about 0.1 to about 20%, preferably from about 0.5 to about 5%, more preferably from about 1 to about 2% by weight.

The following examples will more fully illustrate select embodiments of this invention. All parts, percentages and proportions referred to herein and in the appended claims are by weight unless otherwise indicated.

EXAMPLE 1

A series of solubilization tests were conducted on hydroalcoholic microemulsion compositions to determine the best surfactant. The basic water and oil phases utilized throughout the experiments were as follows.

Water Phase

| INGREDIENTS | WEIGHT % |
|---|---|
| Water | 37 |
| SD-40 Alcohol | 35 |
| Ethyl Lactate | 8 |
| Propylene Glycol | 3 |
| Lactic Acid | 1 |
| Glycolic Acid | 0.5 |
| Salicylic Acid | 0.5 |
| Zinc Sulphate | 0.3 |
| Propylene Glycol | 0.3 |
| α-Hydroxycaprylic Acid | 0.1 |

Oil Phase

| INGREDIENTS | WEIGHT % |
|---|---|
| Vitamin A Palmitate | 0.5 |
| Vitamin E Linoleate | 0.5 |
| Vitamin E Acetate | 0.5 |
| α-Bisabolol | 0.5 |
| Tea Tree Oil | 0.3 |
| Eucalyptus Oil | 0.1 |

The following grading system was used to determine clarity and stability:

0=No emulsion (2 phases)
1=White emulsion, breaks after 24 hours
2=Opaque emulsion, stable
3=Clear microemulsion, clouds after 24 hours
4=Clear microemulsion, stable at 50° C. or 2 months

TABLE 1

| SURFACTANT (all at 4%) | GRADE |
|---|---|
| PEG-2 Oleyl Ether | 0 |
| PEG-20 Oleyl Ether | 1 |
| PEG-10 Oleyl Ether | 1 |
| PEG-10 Oleyl Ether Phosphate | 0 |
| PEG-20 Isocetyl Ether | 0 |
| PEG-40 Stearate | 0 |
| PEG-20 Dilaurate | 0 |
| PEG-20 Glycereth | 1 |
| PEG-7 Glycereth | 1 |
| PEG-45 Palm Kernel Glycerides | 1 |
| PEG-60 Almond Glycerides | 0 |
| PEG-60 Sorbitan Tetraoleate | 0 |
| PEG-21 Stearate | 0 |
| Nonoxynol-9 | 1 |
| Nonoxynol-10 | 1 |
| Nonoxynol-12 | 1 |
| Nonoxynol-15 | 1 |
| Octoxynol-9 | 2 |
| Poloxamer-338 | 3 |
| Poloxamer-407 | 1 |
| Poloxamer-185 | 1 |
| Poloxamer-182 | 1 |
| Poloxamer-331 | 2 |
| Poloxamer-188 | 2 |
| Poloxamer-108 | 1 |
| Poloxamer-131 | 1 |
| Poloxamer-401 | 0 |
| Poloxamer-335 | 0 |
| Nitrol Pen-4612 | 2 |
| Nitrol Pen-4630 | 3 |
| Polysorbate-20 | 0 |
| Polysorbate-60 | 0 |
| Polysorbate-80 | 0 |
| Polysorbate-81 | 0 |
| Polysorbate-85 | 1 |
| Isocetyl PPG-2 PEG-20 Acetate | 1 |
| Procetyl-AWS | 2 |
| PPG-10 Cetyl Ether | 3 |
| PPG-50 Cetyl Ether | 1 |
| PEG-7 Hydrogentated Castor Oil | 1 |
| PEG-35 Hydrogentated Castor Oil | 2 |
| PEG-40 Hydrogentated Castor Oil | 3 |
| PEG-43 Hydrogentated Castor Oil | 2 |
| PEG-54 Hydrogentated Castor Oil | 2 |
| PEG-60 Hydrogentated Castor Oil | 1 |

TABLE II

| COMBINATION SYSTEMS (all at 3% and 3%) | GRADE |
|---|---|
| PEG-40 Hydrogenated Castor Oil (3%) with . . . | |
| PPG-10 Cetyl Ether (1.5%) | 4 |
| PPG-10 Cetyl Ether | 3 |
| PPG-50 Cetyl Ether | 2 |
| PPG-10 Cetyl Ether Phosphate | 2 |
| PEG-6000 Monostearate | 1 |
| Glycereth-7 | 1 |
| Glycereth-26 | 2 |
| Octoxynol-9 | 2 |
| Nonoxynol-100 | 3 |
| PPG-5 Ceteth-20 | 2 |
| Abil Wax 8851 | 2 |
| Abil Wax 8852 | 3 |
| Abil Wax 8873 | 2 |
| Pecosil PS100 | 1 |
| Pecosil PS100ad | 1 |
| Pecosil PS100K | 2 |
| Polysorbate-80 | 2 |
| PPG-10 Butanediol | 4 |
| PPG-12 Buteth-16 | 2 |
| PPG-28 Buteth-35 | 2 |

TABLE II-continued

| COMBINATION SYSTEMS (all at 3% and 3%) | GRADE |
|---|---|
| PPG-9 Buteth-10 | 3 |
| PPG-14 Butyl Ether | 3 |
| Poloxamer-181 | 1 |
| Poloxamer-401 | 2 |
| Poloxamer-338 | 2 |
| PPG-10 Cetyl Ether with . . . | |
| PEG-6000 Monostearate | 1 |
| Glycereth-26 | 2 |
| Glycereth-7 | 3 |
| Poloxamer-338 | 3 |
| Nikkol Pen-4630 | 3 |
| PPG-10 Butyl Ether | 2 |
| PEG-45 Hydrogenated Castor Oil | 2 |
| PEG-54 Hydrogenated Castor Oil | 2 |
| PEG-7 Hydrogenated Castor Oil | 2 |

Based upon the experiments in the above Tables, it is evident that the best combinations are PEG-40 hydrogenated castor oil with either PPG-10 cetyl ether, PPG-10 butanediol or PPG-14 butyl ether.

The foregoing description and examples illustrate selected embodiments of the present invention. In light thereof, various modifications will be suggested to one skilled in the art, all of which are within the spirit and purview of this invention.

What is claimed is:

1. Cosmetic microemulsion compositions which are clear and storage stable comprising:

(i) from about 1 to about 99% of water;

(ii) from about 15 to about 70% of ethanol;

(iii) from about 0.1 to about 3% of skin nutritive oil selected from the group consisting of vitamin oils, $C_{10}$–$C_{60}$ terpenes and mixtures thereof;

(iv) from about 1 to about 10% of castor oil ethoxylated with about 40 to about 55 moles of ethylene oxide per mole of castor oil; and (v) from about 0.1 to about 2.0% of a propoxylated mono- or di-hydric alkanol selected from the group consisting of PPG-10 cetyl ether and PPG-10 butanediol.

2. A composition according to claim 1 wherein the vitamin oils are selected from the group consisting of vitamin A palmitate, vitamin E linoleate, vitamin E acetate and mixtures thereof.

3. A composition according to claim 1 wherein the terpene is a hydrocarbon selected from the group consisting of limonene, pinene, myrcene, caryophyllene, farnesene, lycopene, squalene, zingiberene, carotene, camphene, cedrene and mixtures thereof.

4. A composition according to claim 1 wherein the terpene is an oxygenated terpene selected from the group consisting of geraniol, farnesol, linalool, citronellal, menthol, carvone, camphor, nerol, neral, geranial, thujone, isonorborneol, isoborneol, phytol, bisabolol and mixtures thereof.

5. A composition according to claim 1 wherein water is present in an amount from about 30 to about 60% by weight.

6. A composition according to claim 1 wherein ethanol is present in an amount from about 35 to about 55% by weight.

7. A composition according to claim 1 wherein the ethoxylated castor oil is PEG-40 hydrogenated castor oil.

* * * * *

UNITED STATES PATENT AND TRADEMARK OFFICE
CERTIFICATE OF CORRECTION

PATENT NO. : 5,484,597
DATED      : January 16, 1996
INVENTOR(S): Slavtcheff et al.

It is certified that error appears in the above-indentified patent and that said Letters Patent is hereby corrected as shown below:

On title page, item [54] and col. 1, line 2,

In the title change "HYDROALCHOLIC" to read -- HYDROALCOHOLIC --; and

On title page, item [73], change "Chesebrough-Pond's USA Co.," to read -- Chesebrough-Pond's USA Co., Division of Conopco, Inc. --

Signed and Sealed this

Twenty-sixth Day of March, 1996

Attest:

BRUCE LEHMAN

Attesting Officer        Commissioner of Patents and Trademarks